United States Patent
Krzyzanowski (10) Patent No.: US 6,440,085 B1
(45) Date of Patent: Aug. 27, 2002

(54) METHOD OF ASSEMBLING A NON-METALLIC BIOPSY FORCEPS JAW AND A NON-METALLIC BIOPSY FORCEPS JAW

(76) Inventor: Jacek Krzyzanowski, 17 Oxenden Crescent, Etobicoke Ontario (CA), M9C 4H3

( * ) Notice: Subject to any disclaimer, the term of this patent is extended or adjusted under 35 U.S.C. 154(b) by 0 days.

(21) Appl. No.: 09/878,308

(22) Filed: Jun. 12, 2001

(51) Int. Cl.$^7$ .................................................. A61B 5/00
(52) U.S. Cl. ....................................... 600/564; 606/205
(58) Field of Search ......................... 600/562, 564–567; 606/167, 170, 205–209

(56) References Cited

U.S. PATENT DOCUMENTS

| | | | |
|---|---|---|---|
| 4,721,116 A | * 1/1988 | Schintgen et al. | 600/564 |
| 4,887,612 A | * 12/1989 | Esser et al. | 600/564 |
| 5,238,002 A | * 8/1993 | Devlin et al. | 600/564 |
| 5,535,754 A | * 7/1996 | Doherty | 606/205 |
| 5,647,115 A | 7/1997 | Slater et al. | |
| 6,041,679 A | 3/2000 | Slater et al. | |

* cited by examiner

Primary Examiner—Max Hindenburg
(74) Attorney, Agent, or Firm—Eugene J. A. Gierczak (57) ABSTRACT

A biopsy forceps jaw device and method of assembling, comprising pivotally mounting to a single flat support having a single aperture a threaded, self-centering proximal end and a pointed distal end, an integrally connected non-metallic jaw assembly having a cutting plane. The integrally connected non-metallic jaw assembly pivots about a common axis within the single aperture allowing for rotation of the integrally connected non-metallic jaw assembly within the cutting plane. A pair of actuating wires for moving the integrally connected jaw non-metallic assembly from a closed position to an open position is attached to the integrally connected non-metallic jaw assembly. The threaded self-centering proximal end of single flat support and the pair of actuating wires are inserted into a tubular member. The integrally connected non-metallic jaw assembly and the single flat support are centered within the tubular member through the threaded self-centering proximal end.

8 Claims, 9 Drawing Sheets

METHOD OF ASSEMBLING A NON-METALLIC BIOPSY FORCEPS JAW AND A NON-METALLIC BIOPSY FORCEPS JAW

FIELD OF THE INVENTION

This invention relates in general to method of assembly for a biopsy forceps jaw and a biopsy forceps jaw and more particularly to a method of assembly for a non-metallic biopsy forceps jaw and for the non-metallic biopsy forceps jaw itself used for the removal of tissue samples from a patient.

BACKGROUND OF THE INVENTION

A number of different types of biopsy forceps devices have been developed for taking tissue samples. Some of the biopsy devices take the form of a forceps design with opposing jaws or radial jaws in which the jaws have intermeshing teeth. When activated, the teeth cut the desired tissue and the tissue is stored within the jaw itself. In general these devices have the majority of their design made out of metallic components. This is specifically the case for the biopsy jaw itself. In general the method of assembly for most of these devices requires meticulous effort to align and secure the metallic components of the jaw. This results in costly and time consuming assembly.

The desire to find a less costly and less complicated method of assembly has resulted in the use of some non-metallic components. Examples of prior art methods of assembly and biopsy forceps jaw devices that have been devised to address the aforenoted problems, include, U.S. Pat. No. 6,041,679 issued on Mar. 28, 2000 to Slater. This patent relates to a non-metallic end effector for use in an endoscopic surgical tool includes a metallic core for strength and for providing a selected electrode surface on the end effector. Selectively conductive end effectors are manufactured by insert molding a non-metallic or ceramic or other non-conductive body around a metallic or otherwise conductive core. More specifically, the method of manufacturing includes an end effector for an endoscopic surgical instrument having an actuation means, comprising: forming a metallic skeleton by a process chosen from casting, stamping or photochemically milling; and molding a non-conductive body around said metallic skeleton. The non-conductive body having a proximal end with means for coupling to the actuation means, and a distal end with means for cutting, gripping, clamping, or otherwise contacting tissue.

U.S. Pat. No. 5,647,115 which issued on Jul. 15, 1997, relates to a jaw assembly of an endoscopic biotome is formed by cutting a hemispherical end of a spring metal cylinder with electrical discharge or laser machining equipment to provide opposed jaw cups.

Although the prior art addresses some of the issues described above, it does not address a method of assembly for a non-metallic biopsy forceps jaw device that allows for easy assembly and the use of less costly parts.

SUMMARY OF THE INVENTION

An object of one aspect of the present invention is to provide an improved method of assembly of a non-metallic biopsy forceps jaw device and a non-metallic biopsy forceps jaw.

In accordance with one aspect of the present invention there is provided a method of assembling a biopsy forceps jaw device, comprising pivotally mounting to a single flat support having a single aperture a threaded, self-centering proximal end and a pointed distal end, an integrally connected non-metallic jaw assembly having a cutting plane. The integrally connected non-metallic jaw assembly pivots about a common axis within the single aperture allowing for rotation of the integrally connected non-metallic jaw assembly within the cutting plane. A pair of actuating wires for moving the integrally connected jaw non-metallic assembly from a closed position to an open position are attached to the integrally connected non-metallic jaw assembly. The ribbed proximal end of single flat support and the pair of actuating wires are inserted into a tubular member. The integrally connected non-metallic jaw assembly and the single flat support are centered within the tubular member through the threaded self-centering proximal end.

Conveniently, the integrally non-metallic jaw assembly may be an upper jaw and a lower jaw, wherein a cutting edge is insert molded and/or snap-connected to the lower jaw for cutting tissue. The upper and lower jaws may be snap-connected to one another.

Preferably, the threaded self-centering proximal end of the single flat support may be screwed into the tubular member thereby self-centering the jaw assembly in the tubular member.

In accordance with another aspect of the present invention there is provided a non-metallic flexible biopsy jaw assembly for a biopsy forceps device which may be inserted through an endoscope for the removal of body tissue from a body cavity, comprising a tubular member, a single flat support having a single aperture and a threaded, self-centering proximal end and a pointed distal end. The proximal end is screwed directly into the tubular member and the single flat support is self-centered within the tubular member.

An integrally connected non-metallic jaw assembly having a cutting plane is mounted pivotally about a common axis within the single aperture of the single flat support for rotation of the integrally connected jaw assembly within the cutting plane of the integrally connected jaw assembly. A pair of actuating wires are snap-connected to the integrally connected jaw assembly and are slidable relative to the tubular member and the single flat support for moving the integrally connected jaw assembly from a closed position to a open position when activated.

Advantages of the present invention include the use of non-metallic materials for the biopsy jaws thereby allowing the snap-connections of the upper and lower jaws and the actuating wires into the jaws. Furthermore, the proximal end of the single flat support is treaded in such a way that the support alone self centers the jaw assembly within the tubular member. The assembly of the device in conjunction with the components is such that it is not costly, as well as reducing the overall time required for assembly. Furthermore, the use of non-metallic components makes the device cheaper and therefore disposable if desired.

BRIEF DESCRIPTION OF THE DRAWINGS

A detailed description of the preferred embodiments are provided herein below by way of example only and with reference to the following drawings, in which.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 1:
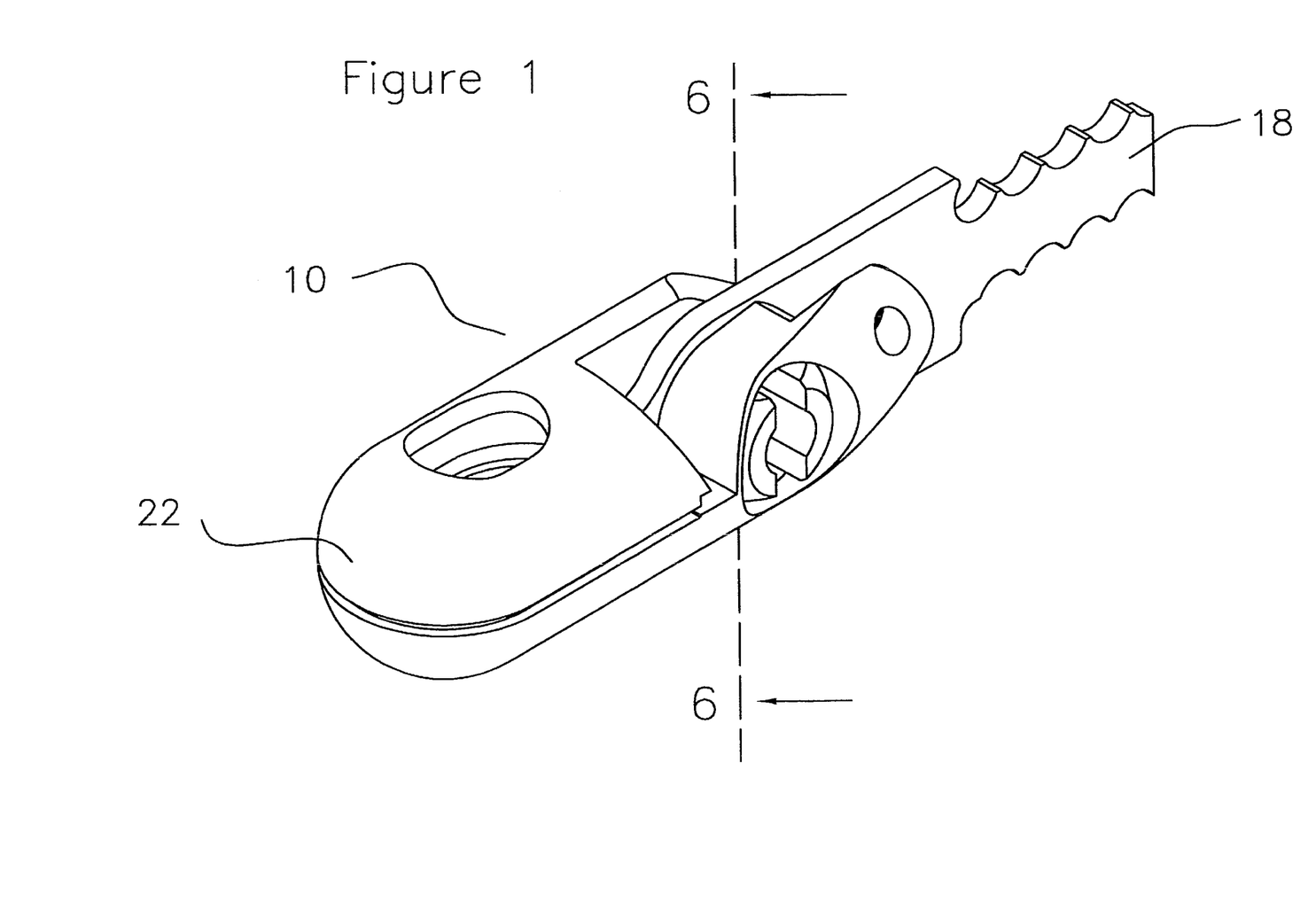
FIG. 1 in a perspective view, illustrates a non-metallic biopsy forceps jaw in accordance with a preferred embodiment of the present invention.
Figure 2:
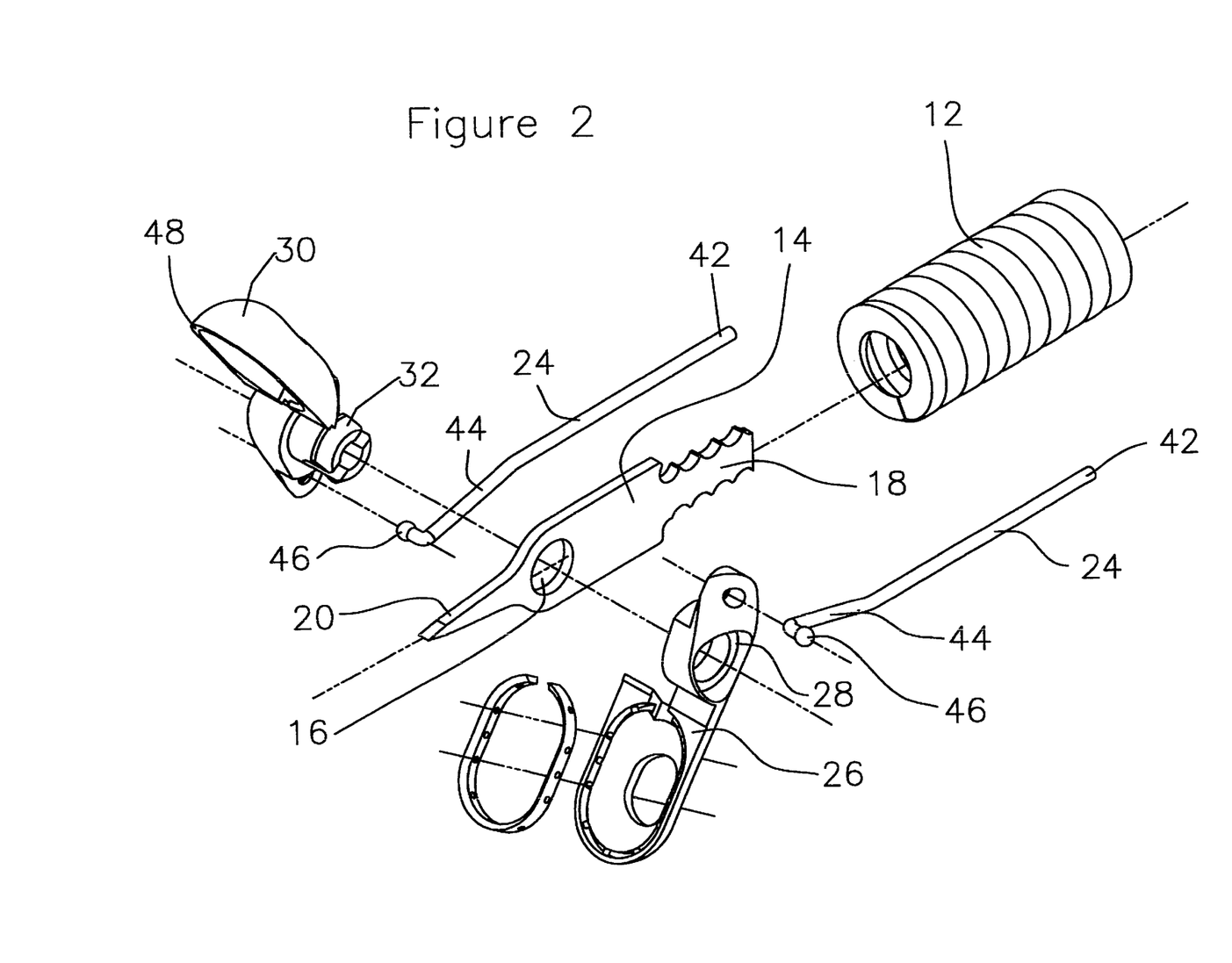
FIG. 2 in an exploded view, illustrates the non-metallic biopsy forceps jaw of FIG. 1.

Referring to FIGS. 1 and 2, there is illustrated in a perspective and exploded views, a non-metallic flexible biopsy jaw assembly for a biopsy forceps device which may be inserted through an endoscope for the removal of body tissue from a body cavity in accordance with a preferred embodiment of the present invention. The non-metallic flexible biopsy jaw assembly 10 includes a tubular member 12 and a single flat support 14. The single flat support 14 has a single aperture 16, a threaded, self-centering proximal end 18 and a pointed distal end 20. The threaded self-centering proximal end 18 of the single flat support 14 may be screwed directly into the tubular member 12. The threaded self-centering proximal end allows for the single flat support and the non-metallic flexible biopsy jaw assembly 10 to be self-centered within the tubular member 12.

The non-metallic flexible biopsy jaw assembly 10 further includes an integrally connected non-metallic jaw assembly 22. The integrally connected non-metallic jaw assembly 22 has a cutting plane and is mounted pivotally about a common axis within the single aperture 16 of the single flat support 14 for rotation of the integrally connected non-metallic jaw assembly 22 within the cutting plane of the integrally connected non-metallic assembly 22. A pair of actuating wires 24 are snap-connected to the integrally connected non-metallic jaw assembly 22 and are slidable relative to the tubular member 12 and the single flat support 14. The actuating wires 24 move the integrally connected non-metallic jaw assembly 22 from a closed position to an open position when activated.

Figure 3:
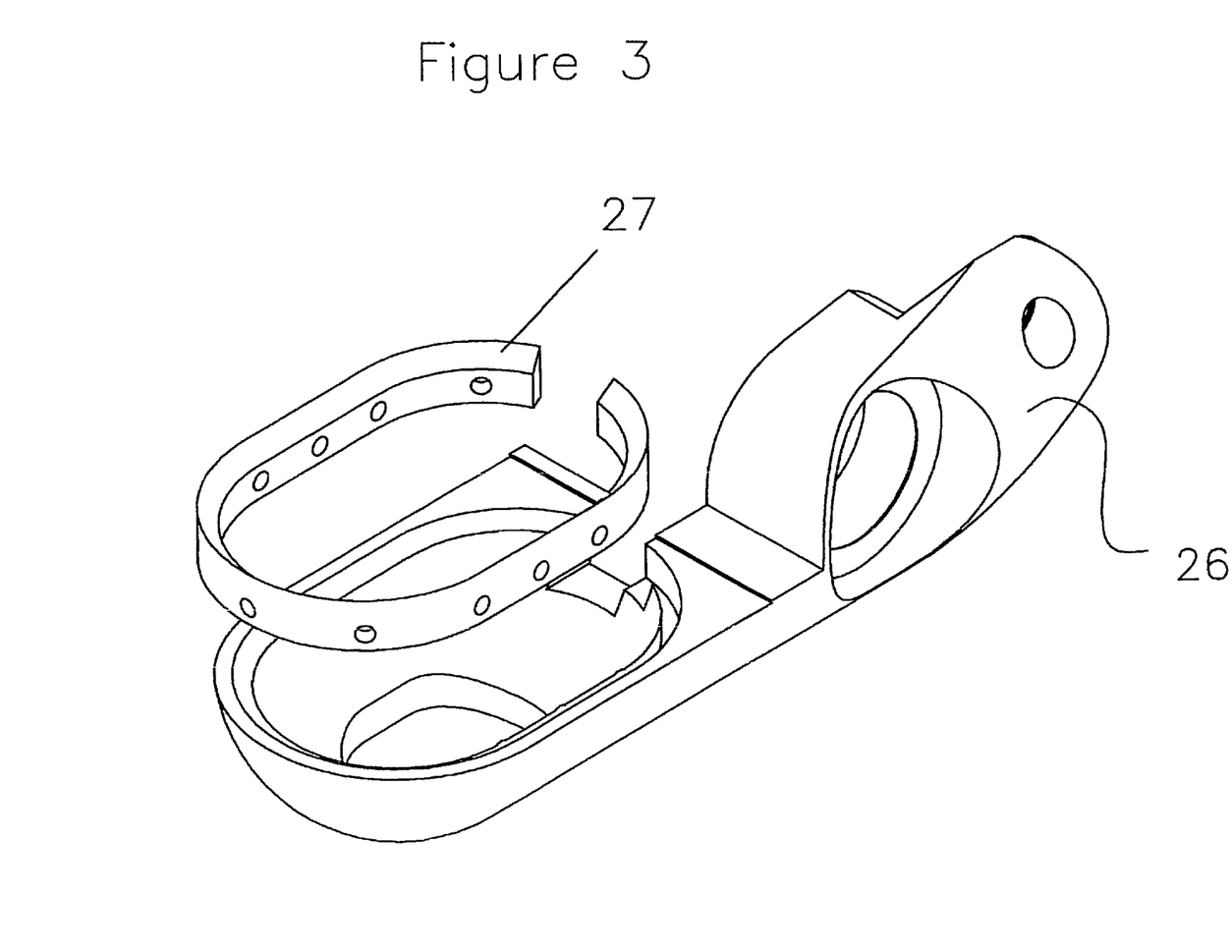
FIG. 3 in a n exploded view, illustrates the lower jaw of the non-metallic biopsy forceps jaw.
Figure 4:
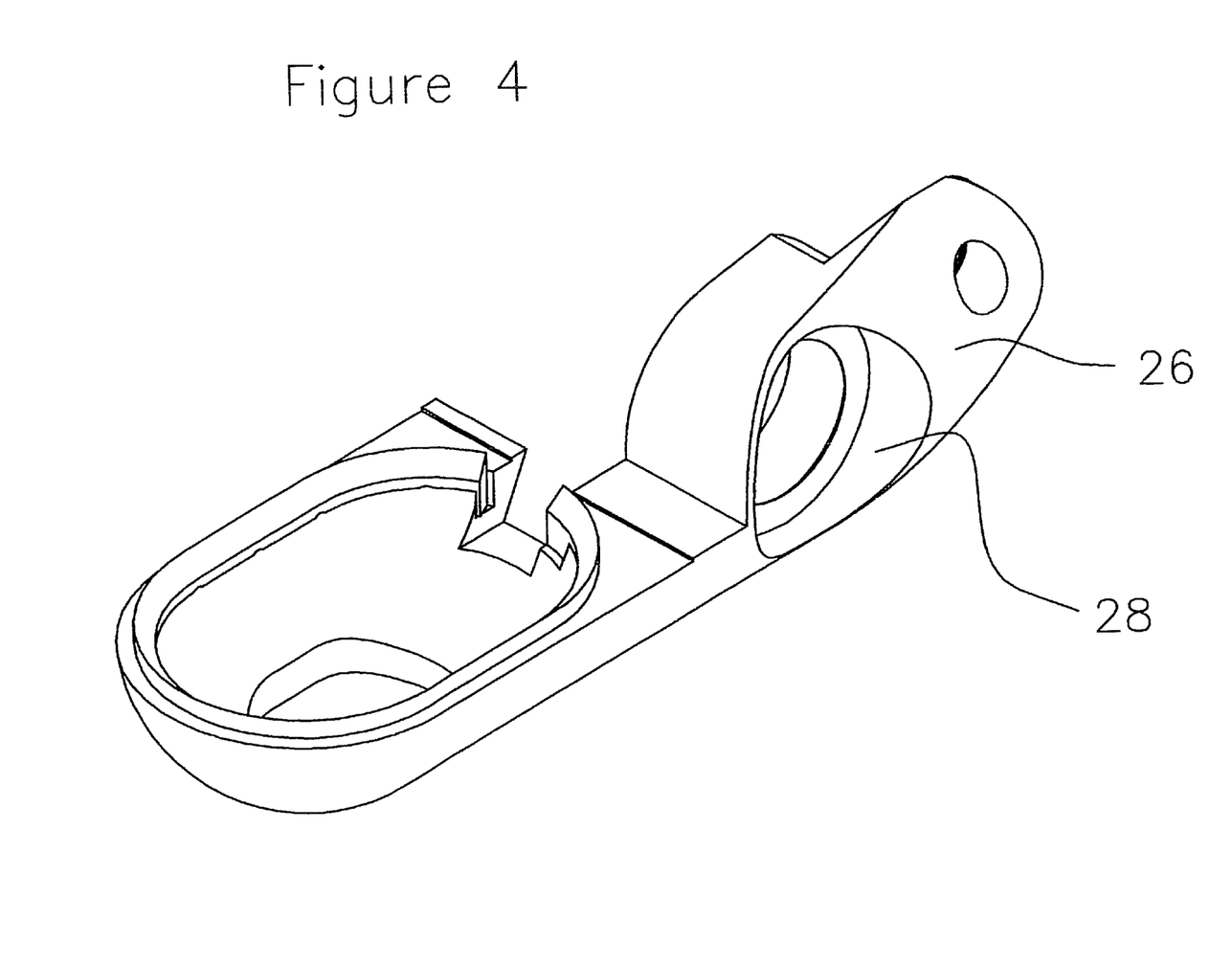
FIG. 4 in a perspective view, illustrates the lower jaw of non-metallic biopsy forceps jaw of FIG. 1.
Figure 5:
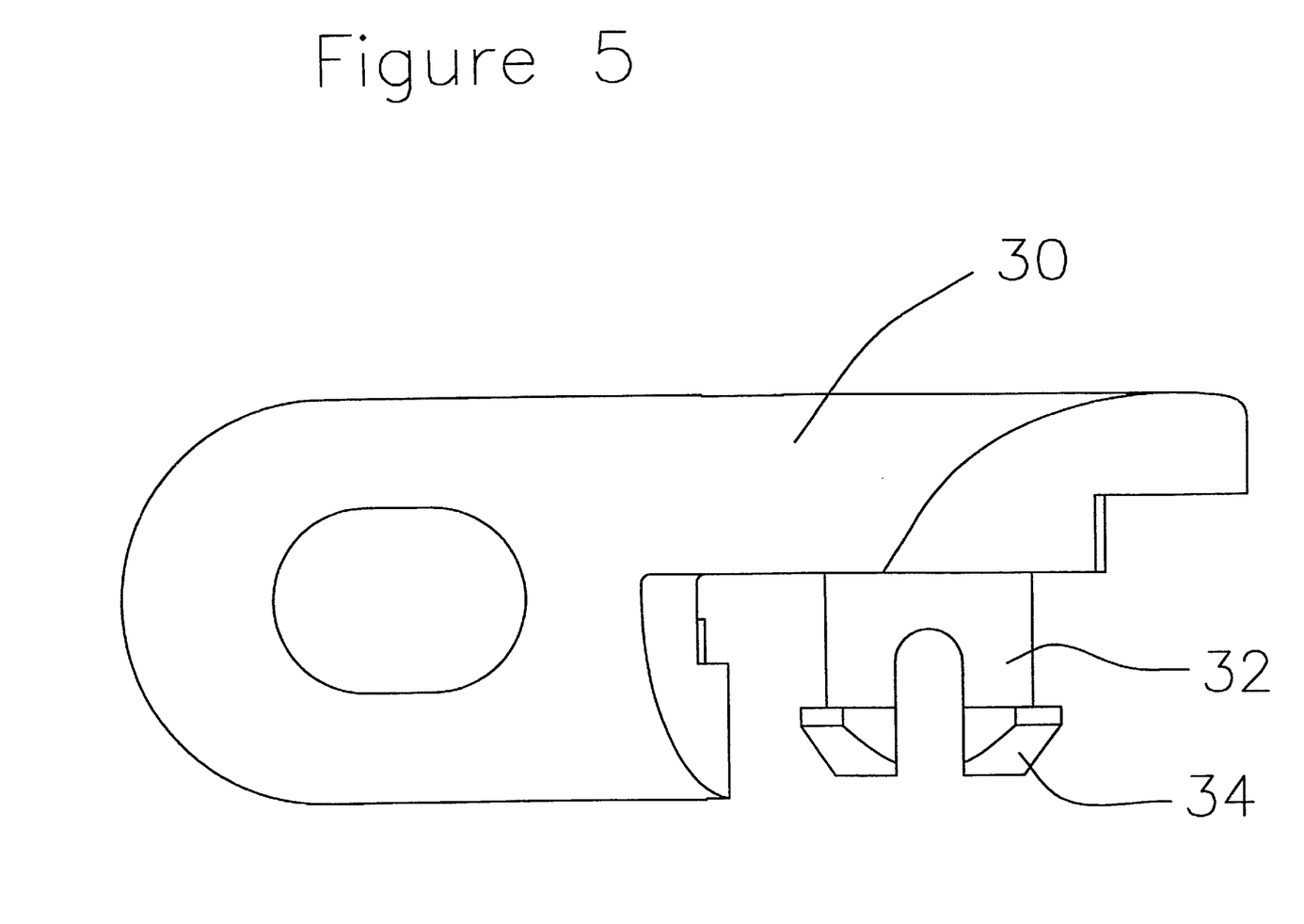
FIG. 5 in a top view, illustrates the upper jaw of the non-metallic biopsy forceps jaw of FIG. 1.

Referring to FIG. 3, the integrally connected non-metallic jaw assembly 22 may be further defined as a lower jaw 26 and a upper jaw 30. The lower jaw 26 may further comprise of a cutting edge 27. The cutting edge 27 may be metal blade or insert that is insert molded and/or snap-connected into the lower jaw 26.

Referring to FIGS. 4, 5 and 6a–c, the integrally connected non-metallic jaw assembly 22 further includes a single stepped pivot hole 28 in the lower jaw 26, and a flexible pin 32 in the upper jaw 30. The flexible pin 32 of the upper jaw 30 passes through the single aperture 16 of the single flat support member 14 and is snap-connected to the stepped pivot hole 28 of the lower jaw 26.

Figure 6A:
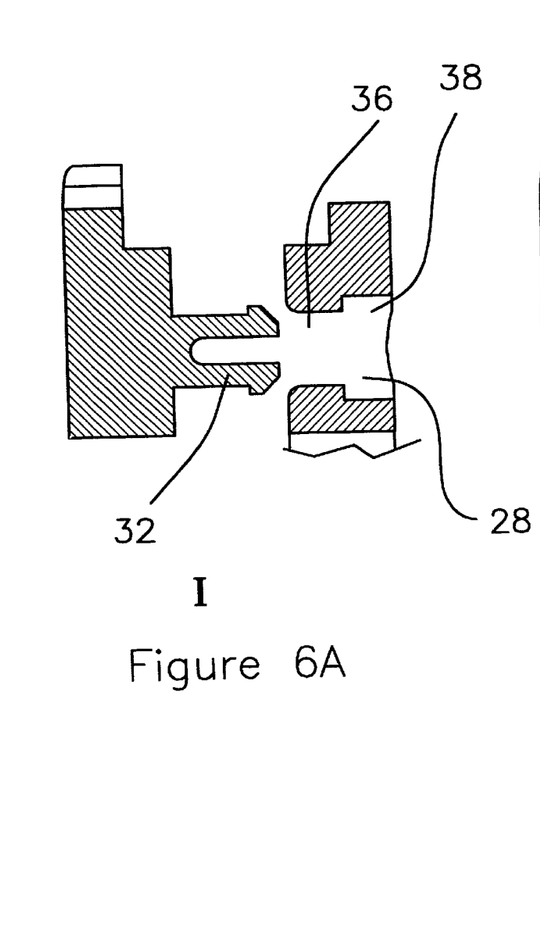
FIGS. 6a–c in a cross sectional views taken along the line 6—6, illustrates the snap-connection of the upper and lower jaws of the non-metallic biopsy forceps jaw of FIG. 1.
Figure 6B:
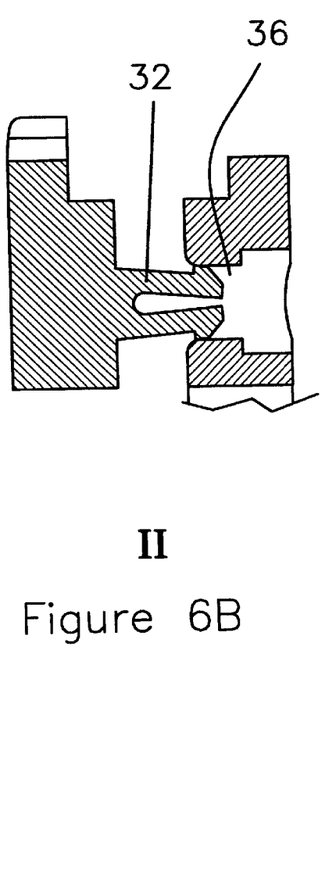
Figure 6C:
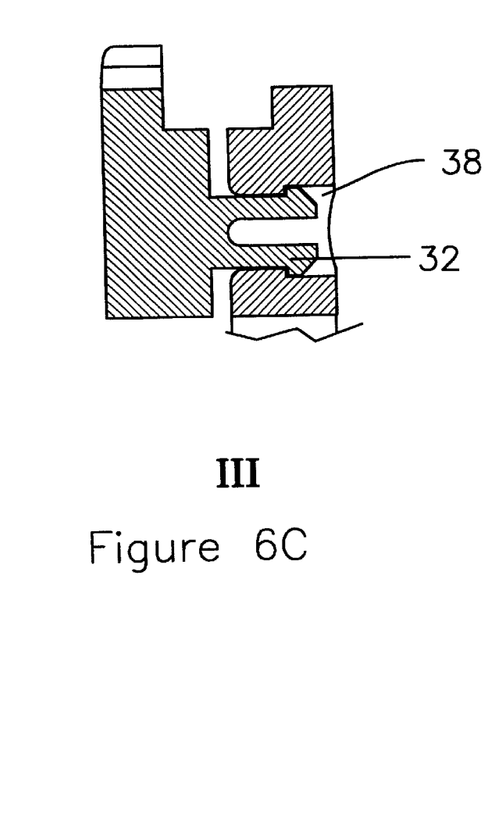

The flexible pin 32 may have a pronged and shaped end 34 for engagement within the stepped pivot hole 28. The stepped pivot hole 28 has a narrow entrance 36 into the stepped pivot hole 28 and a wider portion 38. The pronged and shaped end 34 of the flexible pin 32 flexes and engages the narrow entrance 36 and registers with the wider portion 38 of the stepped pivot hole 28.

Figure 7:
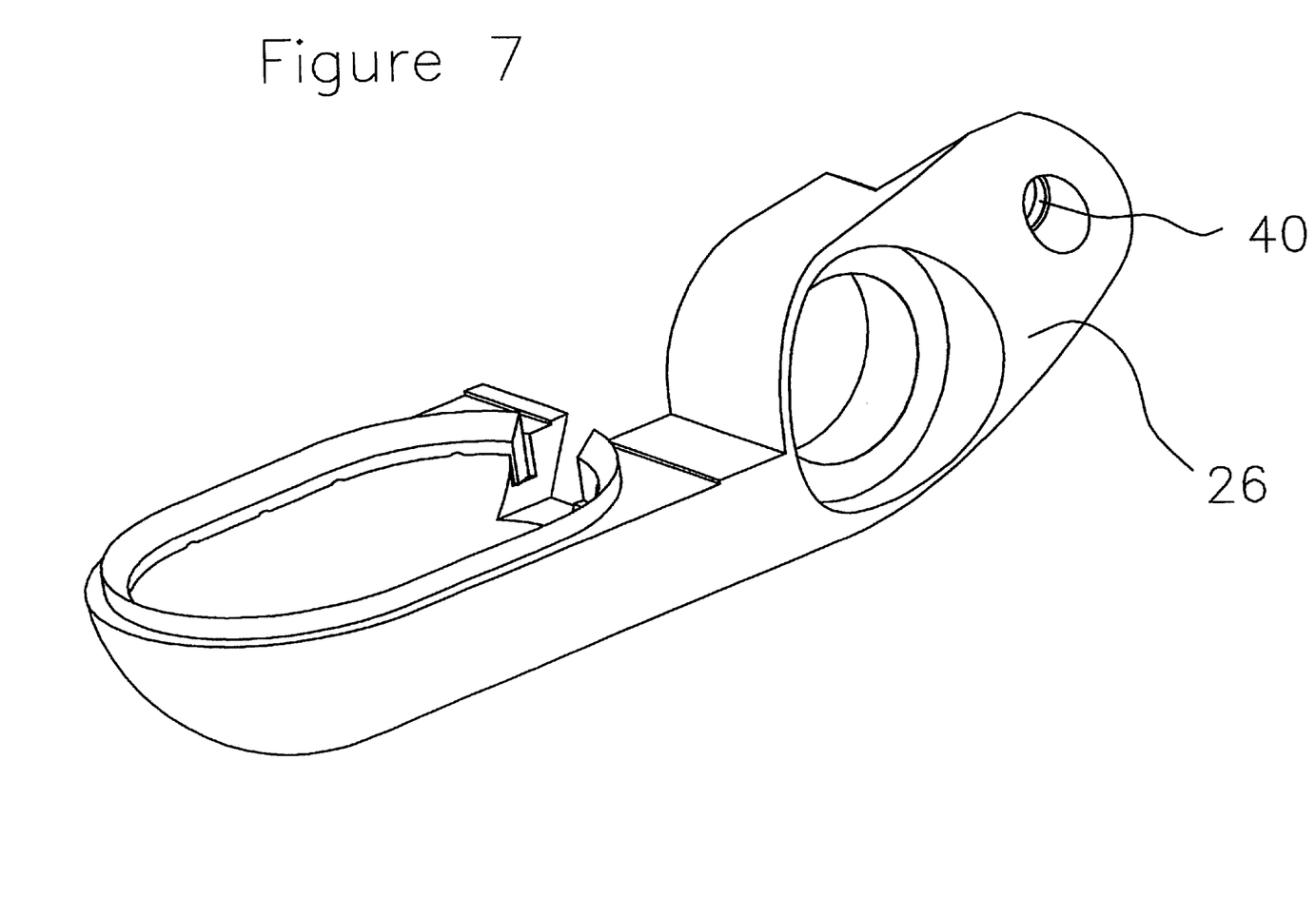
FIG. 7 in a perspective view, illustrates the lower jaw of non-metallic biopsy forceps jaw of FIG. 1.

Referring to FIG. 7, the integrally connected non-metallic jaw assembly 22 further includes a stepped aperture 40 in each of the lower and upper jaws 26 and 30. Referring to FIG. 2, the actuating wires 24 further comprise of distal ends 42 that are inserted through the tubular member 12, and proximal ends 44 having shaped protuberances 46. The shaped protuberances 46 of the actuating wires 24 register within the stepped apertures 40 of the lower and upper jaws 26 and 30 in a snap-connection.

Figure 8:
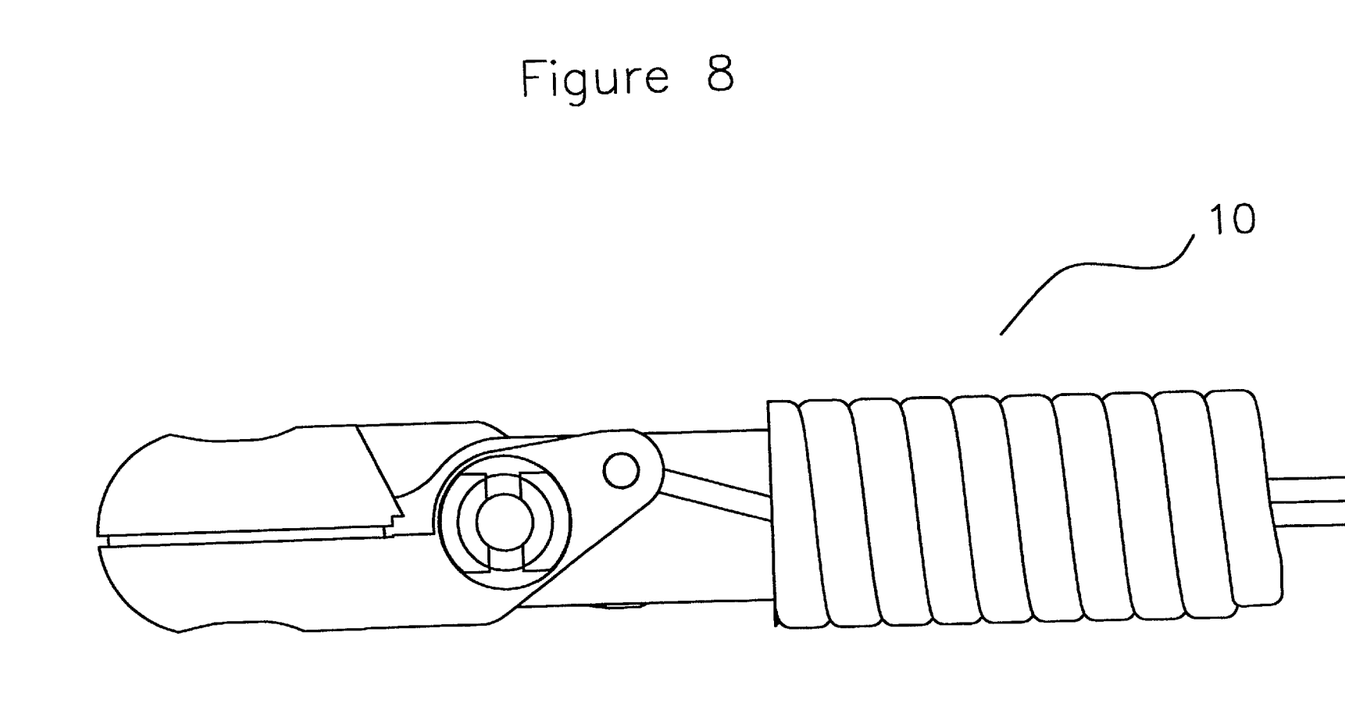
FIG. 8 in a side elevational view, illustrates the non-metallic biopsy forceps jaw of FIG. 1 in a closed position.
Figure 9:
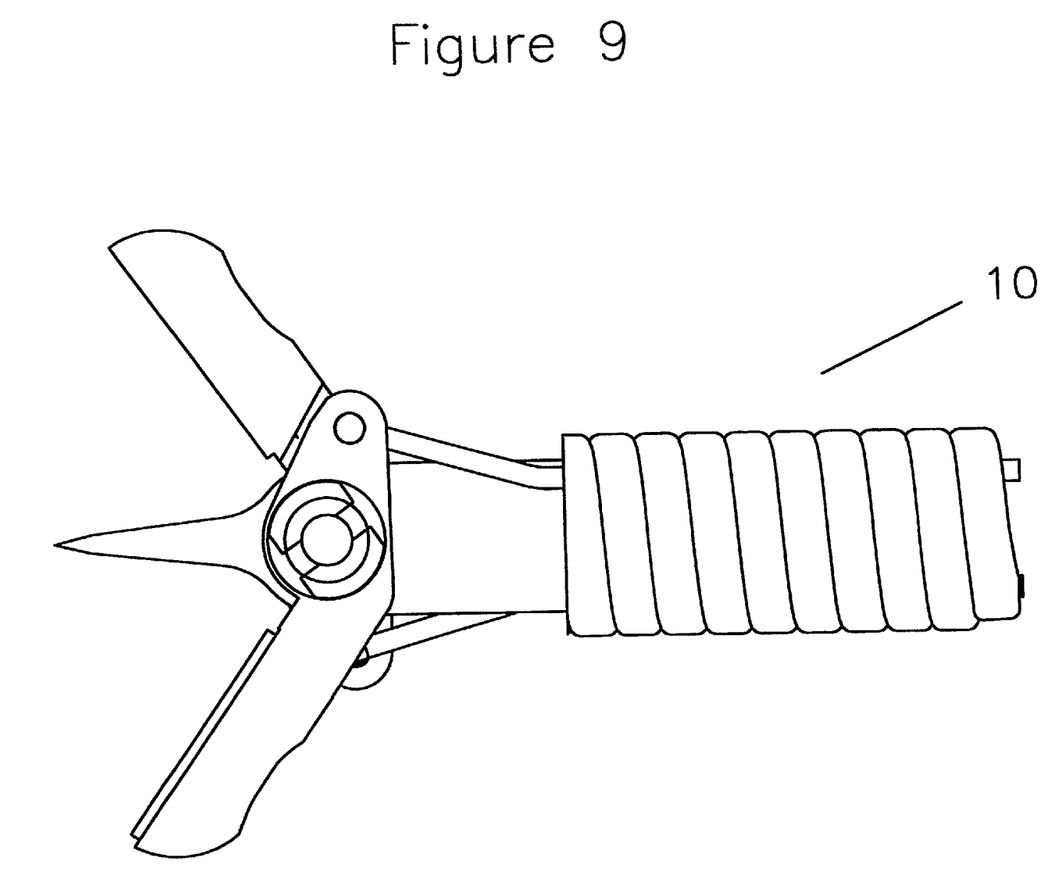
FIG. 9 in a side elevational view, illustrates the non-metallic biopsy forceps jaw of FIG. 1 in an open position.

Referring to FIGS. 2, 8 and 9, there is illustrated in accordance with another preferred embodiment of the present invention, a method of assembling a Non-metallic biopsy forceps jaw device 10. The method of assembly includes pivotally mounting to the single flat support 14 through the single aperture 16 of the single flat support 14, the integrally connected non-metallic jaw assembly 22. The integrally connected non-metallic jaw assembly 22 can pivot about the common axis within the single aperture 16 allowing for rotation of the integrally connected non-metallic jaw assembly 22 within the cutting plane.

The integrally connected non-metallic jaw assembly 22, and more specifically the lower and upper jaws 26 and 30, are snap-connected to one another, by passing the flexible pin 32 of the upper jaw 30 through the single aperture 16 and registering the flexible pin 32 within the stepped pivot hole 28 of the lower jaw 26. The snap-connection between the upper and lower jaws 30 and 26 allows easy assembly of the device 10.

The pair of actuating wires 24 for moving the integrally connected jaw non-metallic assembly 22 from a closed position to an open position are snap-connected to the upper and lower jaws 30 and 26. Specifically, the shaped protuberances 46 of the actuating wires 24 register within the stepped apertures 40 of the upper and lower jaws 30 and 26 in a similar fashion to that described for the connection between the upper and lower jaws 30 and 26.

The threaded self-centering proximal end 18 of single flat support 14 and proximal ends 42 of the pair of actuating wires 24 are inserted into the tubular member 12. The integrally connected non-metallic jaw assembly 22 and the single flat support 14 are centered within the tubular member 12 through the threaded self-centering proximal end 18 of the single flat support 14. The threaded self-centering proximal end 18 of the single flat support 14 is screwed into the tubular member 12 thereby self-centering the entire jaw assembly 10 in the tubular member 12. The tubular member 12 may be either flexible or rigid.

As discussed above the integrally non-metallic jaw assembly may be an upper jaw 30 and a lower jaw 26, wherein a edge 27 may be insert molded and/or snap-connected into the lower jaw 26. The cutting edge 27 may be inserted for enhanced cutting of the tissue. Specifically, the present invention allows for the sharp, cutting edge 27 of the lower jaw 26 to contact the dull edge 48 of the upper jaw 30 in a similar fashion as seen with the use of a knife on a cutting board. This arrangement therefore avoids the difficulties seen with radial jaws and the need for perfect alignment for the intermeshing teeth to effectively cut the tissue.

Other variations and modifications of the invention are possible. All such modifications or variations are believed to be within the sphere and scope of the invention as defined by the claims appended hereto.

I claim:

1. A non-metallic biopsy jaw assembly for a biopsy forceps device which may be inserted through an endoscope for the removal of body tissue from a body cavity, comprising:
   (a) a tubular member;
   (b) a single flat support having a single aperture, a threaded self-centering proximal end and a pointed distal end wherein said proximal end is screwed directly into said tubular member and said single flat support is self-centered within said tubular member;
   (c) an integrally connected non-metallic jaw assembly having a cutting plane and mounted pivotally about a common axis within said single aperture for rotation of said integrally connected jaw assembly within said cutting plane of said integrally connected jaw assembly;
   (d) a pair of actuating wires snap-connected to said integrally connected jaw assembly and slidable relative to said tubular member and said single flat support for moving said integrally connected jaw assembly from a closed position to a open position when activated.

2. A non-metallic biopsy jaw assembly as claimed in claim 1 wherein said integrally connected non-metallic jaw assembly is defined as a lower jaw and an upper jaw, and further comprising inserting into said lower jaw a cutting edge.

3. A non-metallic biopsy jaw assembly as claimed in claim 2 wherein said cutting edge is metal blade or insert that is insert molded and/or snap-connected into said lower jaw.

4. A biopsy jaw assembly as claimed in claim 2, wherein said lower jaw further comprises a single stepped pivot hole and a upper jaw having a flexible pin wherein said flexible pin of said upper jaw passes through said aperture of said single flat support member and is snap-connected to said stepped pivot hole of said lower jaw.

5. A biopsy jaw assembly as claimed in claim 4, wherein said flexible pin has a pronged and shaped end for engagement within said stepped pivot hole.

6. A biopsy jaw assembly as claimed in claim 5, wherein said stepped pivot hole has a narrow entrance into said stepped pivot aperture and a wider portion, whereby said pronged and shaped end of said flexible pin flexes and engages said narrow entrance and registers with said wider portion of said stepped pivot aperture.

7. A biopsy jaw assembly as claimed in claim 6 wherein said lower and upper jaws each have a stepped aperture.

8. A biopsy jaw assembly as claimed in claim 7 wherein said actuating wires further comprise distal ends that are inserted through said tubular member, and proximal ends having shaped protuberances whereby said shaped protuberances of said actuating wires register within said stepped apertures of said lower and upper jaws in a snap-connection.

* * * * *